United States Patent [19]
Gordon

[11] Patent Number: 5,533,342
[45] Date of Patent: Jul. 9, 1996

[54] SEMI-AUTOMATED CRYOSTAT

[76] Inventor: Abe Gordon, 512 Warwick Ave., Teaneck, N.J. 07666

[21] Appl. No.: 386,814

[22] Filed: Feb. 8, 1995

[51] Int. Cl.$^6$ .................... F25B 19/00; F25C 5/02; G01N 1/06; B26D 7/08
[52] U.S. Cl. .................... 62/51.1; 62/320; 83/915.5
[58] Field of Search .................... 62/320, 51.1; 83/915.5

[56]  References Cited

U.S. PATENT DOCUMENTS

| | | |
|---|---|---|
| 3,203,290 | 8/1965 | Ashby . |
| 3,204,424 | 9/1965 | McCormick et al. . |
| 3,218,896 | 11/1965 | McCormick . |
| 3,233,965 | 2/1966 | McCormick et al. . |
| 3,236,133 | 2/1966 | DePas . |
| 3,296,821 | 1/1967 | Malinin . |
| 3,456,538 | 7/1969 | Barton et al. . |
| 3,462,969 | 8/1969 | Grasenick . |
| 3,495,490 | 2/1970 | Dollhopf . |
| 3,680,420 | 8/1972 | Blum . |
| 3,768,273 | 10/1973 | Missimer . |
| 4,012,475 | 3/1977 | Kindel .................... 83/915.5 X |
| 4,162,677 | 7/1979 | Gregory . |
| 4,492,139 | 1/1985 | Forsström et al. .................... 83/915.5 X |
| 4,695,339 | 9/1987 | Rada . |
| 4,752,347 | 6/1988 | Rada . |
| 4,840,034 | 6/1989 | Liberman . |
| 4,840,035 | 6/1989 | Liberman . |
| 5,048,300 | 9/1991 | Lihl .................... 83/915.5 X |
| 5,070,935 | 12/1991 | Sitte et al. .................... 62/49.2 X |
| 5,156,019 | 10/1992 | McCormick . |
| 5,255,585 | 10/1993 | Gordon . |
| 5,282,404 | 2/1994 | Leighton et al. .................... 83/915.5 X |

FOREIGN PATENT DOCUMENTS

| | | |
|---|---|---|
| 1336892 | 11/1973 | United Kingdom . |
| 9305936 | 4/1993 | WIPO . |

OTHER PUBLICATIONS

APD Cryogenics Inc., Cryotiger™I, Jul. 1994, U.S.A.
Instrumedics, Inc., Cryostat Frozen Sectioning Aid, U.S.A.
Instrumedics, Inc., More Products From Instrumedics, U.S.A.
Bianchi et al., "Accuracy and Reliability of Frozen Section Diagnosis in a Series of 672 Nonpalpable Breast Lesions", Feb. 1995, Am. J. Clin. Path.
Cryostar®–95° C Ultra–Low Temperature Freezers.

Primary Examiner—Christopher Kilner
Attorney, Agent, or Firm—John R. Mugno

[57]  ABSTRACT

The present invention provides a system and method for freezing and cutting a tissue specimen for medical diagnostic purposes which comprises a specimen block holder for holding the tissue specimen; an embedding medium; a freezing plane for providing direct metal contact freezing of the specimen; a knife blade comprising a cutting edge which is substantially parallel to and may be displaced a preset distance from the freezing plane; a block holder for holding the specimen; and driving means for transporting the block holder towards the freezing plane for creating a flat frozen surface of the specimen having a thickness t and also for transporting the frozen specimen past the knife edge to provide a section having a desired thickness. The planar relationship and known distance between the freezing plane and the cutting edge together will be used as the basis for calculating frozen thickness t of the specimen. This allows for precise and automated movement of the block holder for trimming. The freezing plane is preferably cooled by means of first and second refrigerants which are capable of being stored in a single compressor. The use of two mating wedge washers are preferably provided at the freezing block to insure a proper parallel orientation between the cutting edge and the freezing plane.

39 Claims, 9 Drawing Sheets

SEMI-AUTOMATED CRYOSTAT

FIELD OF INVENTION

This invention is generally directed to the field of the snap-freezing of a tissue specimen and surrounding embedding medium and the cutting of a thin section of such specimen for microscopic examination. More particularly, this invention is directed to a cryostat which both freezes and cuts a section of a tissue specimen in a single chamber with minimal manual intervention and a high degree of precision.

BACKGROUND OF THE INVENTION

As used in histology, a cryostat is a cooled chamber which is used to freeze a tissue specimen. The cryostat chamber is capable of maintaining a constant low temperature, typically by means of mechanical refrigeration. A specimen sample such as body tissue, bone, teeth, or sections of entire body organs are frequently desired to be frozen, then cut to a thin uniform thickness, to examine microscopically.

Examples of prior art cryostats are shown, for example, in U.S. Pat. Nos. 3,680,420; 4,840,035; 4,840,034; 3,495,490; and 3,462,969. Each of these prior art devices has shortcomings as will be generally discussed below.

In a typical prior art procedure for freezing, cutting and preparing a surgical specimen for microscopic examination, the tissue sample is brought into the laboratory for diagnosis while the patient is still on the operating table. Thus, as can be easily appreciated, it is essential to freeze, cut, and diagnose the section of tissue specimen as quickly as possible. Any unnecessary delays can be life threatening. In order to minimize the time required to perform the critical steps of freezing, cutting and diagnosis of a tissue section, an embedding medium (e.g., an aqueous solution, a viscous aqueous solution, or a viscous aqueous gel) is dispensed onto a specimen holder or block holder which is usually in the form of a small metal block. The specimen is either placed on top of or submerged into the embedding medium, and then is frozen by any number of means. In most prior art cryostats, the tissue specimen holder is placed on a cold shelf (the freezing shelf) where the medium and tissue specimen are frozen. Alternatively, a small heat extractor which has been equilibrated to the freezer shelf temperature, may be used to flatten and freeze the tissue specimen. Yet another technique may be used in which the entire specimen holder with the medium and tissue specimen in place, may be immersed in iso-pentane which is either chilled in a dry-ice bath or liquid nitrogen. In still another technique, direct immersion in liquid nitrogen may be used. As can be appreciated, regardless of the freezing technique incorporated, it is generally desirable that the tissue be frozen at the lowest possible temperature (and therefore as quickly as possible) since more rapid freezing results in the formation of smaller ice crystals, and therefore, less damage to the tissue morphology. Also, since the tissue itself is a poor thermal conductor, the best frozen tissue to examine is the tissue at the surface closest to the cooling source. The tissue layers which are further from the surface freeze more slowly (due to the low thermal conductivity of tissue) and therefore have larger ice crystals and poorer quality tissue morphology.

While certain cooling agents such as liquid nitrogen provide relatively rapid freezing, due to its boiling point of −196° C., a thermal conductivity problem arises since the liquid will immediately become a gas upon contact with the tissue specimen. For this reason, direct metallic contact, when used as a means of freezing tissue, has been demonstrated as being superior to liquid immersion because of the higher thermal conductivity of metals compared to liquids. This direct metallic contact freezing technique is used in a snap-freezing device sold under the tradename "Gentle Jane" by Instrumedics, Inc. of Hackensack, New Jersey. The freezing plane of a chilled heat extractor is brought in contact with the specimen and surrounding gel and almost instantaneously freezes and flattens the sample.

During the freezing process a complex set of rapid events takes place during which time water is pulled out of the cellular material to form ice crystals. This transport of water dries out the cellular material (dehydration). As the ice-crystals form, their growth displaces the adjacent cellular material. In addition, the ice crystals, which have microscopic points and edges, can also puncture and/or cut the cell membranes. The slower the ice crystal formation (slow freezing) the more time there is for crystals to grow in size. As a result, there is considerable displacement of the original tissue architecture grossly and microscopically. In the conventional section retrieval method whereby the tissue section is melted, the melting ice crystals rehydrate the cells in a random manner thereby obliterating the original detail inherent in the cell. In those cells whose membranes have been damaged, there may be an additional outflow of fluids which causes collapse of the cell.

By contrast, very rapid or snap-freezing converts the identical amount of water into ice except the ice crystals form very rapidly and as a result are very small. Under ideal conditions in which the tissue is snap-frozen at 196° C. and the uppermost section is retrieved, the ice crystals are so small that even under magnification of 1,000 times they are difficult to detect. Under these conditions, the ice crystal damage visually blends into the background of the cell structure.

The retrieval of a snap-frozen section at or very close to the freezing plane begins to approach the ideal. Heretofore it was not possible to do this. Typically, the section that is retrieved is deeper in the specimen where its freezing rate was much slower. Consequently the ice crystals are larger and the damage greater. The primary virtue of this freezing method in addition to its speed and level of automation is the ability to acquire a snap-frozen section at or close to the freezing plane.

After the tissue specimen has been frozen on the block holder, it is then manually clamped in a vice-like mechanism of a microtome apparatus. Through a series of synchronized physical movements, the microtome blade is used to cut the tissue specimen. The thickness of the individual sections attainable range typically between two microns and twenty-five microns.

In practice, before the actual cutting takes place, it is necessary to align the frozen surface of the tissue to the cutting plane defined by the knife edge. This step typically requires a cumbersome manual trial and error procedure requiring considerable patience and skill. The knife holder is temporarily unclamped and repositioned either closer to or further away from the frozen surface of tissue and then reclamped. The operator then makes a test cut to determine if further adjustment is necessary. The process is repeated as often as necessary until the frozen surface is positioned at the knife edge within acceptable limits.

During the normal trimming sequence, the uppermost layers of tissue are trimmed away in order to obtain a flat surface with a completely exposed tissue face. Even when the aforementioned direct metallic heat extractor technique is used, and a flat surface results, the freezing plane may not be coincident with the cutting plane of the microtome, thus requiring significant trimming before a desired flat specimen face is achieved. The need for additional trimming sequences not only results in the need to remove additional debris (which can be performed by the vacuum system described in U.S. Pat. No. 5,255,585) and additional time delays, but would also result in a poorer quality section for diagnosis since, as described previously, tissue sections further from the surface generally suffer greater morphological damage due to the slower freezing of these surface sections than those sections closer to the cold surface.

If there is a large angular misalignment between the freezing plane in the cryostat and the cutting plane of the microtome, the operator may have to realign the clamping of the block to bring the freezing plane into closer alignment with the cutting plane. After realignment of the block, the trimming sequence is repeated until a new smooth surface is attained. This block holder realignment and trimming of the block face can be the most time consuming step of the entire process thus potentially jeopardizing the well being of the patient.

Additional delays in the process often result due to the need to "tease" the cut section away from the block face and flatten it on the surface of the knife (i.e., the brush method). Alternatively, the "anti-roll-plate" method can be used in which a flat plate is positioned to create a gap into which the cut section can advance, thus reducing curling. Unfortunately, both methods are operator sensitive, requiring a skillful hand. Also, the thinner the section, the more fragile the step becomes, making flattening and handling even more difficult. Once an appropriate thin section of the specimen has been obtained, the next step is to mount it on a slide. This step is usually accomplished by touching the frozen section with a room-temperature microscope slide thereby instantaneously melting the section. Capillary forces adhere the section to the slide. The section on the slide is then usually dried, frozen, stained and cover-slipped to prepare it for microscopic examination.

It can be appreciated that the prior art does not provide a fast and effective technique for freezing, cutting, and examining a thin section of a tissue specimen for medical diagnostic purposes. All of the prior art devices require an undesirable amount of skilled manual handling of the tissue specimen which results in unreasonable delays. The problem is compounded by the poor morphological detail of relatively slow frozen tissue, making it difficult to give an unequivocal diagnosis.

It is therefore an object of the present invention to provide a new, faster, and improved system and method for freezing and cutting a tissue specimen for medical diagnostic purposes.

It is therefore another object of the present invention to provide a new and improved system and method of freezing and cutting a tissue specimen for medical diagnostic purposes which performs both the snap-freezing and cutting steps in a single chamber.

It is yet another object of the present invention to provide a new and improved system and method of freezing and cutting a tissue specimen for medical diagnostic purposes which minimizes manual handling of said tissue specimen.

It is a further object of the present invention to provide a new and improved system and method of freezing and cutting a tissue specimen for medical diagnostic purposes which minimizes the amount of trimming required to be made by the operator to obtain an appropriate section for examination.

It is still another object of the present invention to provide a new and improved system and method of freezing and cutting a tissue specimen for medical diagnostic purposes which freezes the tissue specimen in a manner which results in a minimal time delay and reduced ice crystal damage due to the smaller ice crystal size.

It is still a further object of the present invention to provide a new and improved system and method of freezing and cutting a tissue specimen for medical diagnostic purposes which provides an appropriate tissue section with a minimal amount of trimming.

It is still another object of the present invention to provide a new and improved system and method of freezing and cutting a tissue specimen for medical diagnostic purposes which provides an appropriate tissue section with a large specimen face.

Further objects and advantages of the present invention will become apparent as the following description proceeds.

SUMMARY OF THE INVENTION

The present invention provides a system and method for freezing and cutting a tissue specimen for medical diagnostic purposes which comprises a specimen block holder already stated for holding the tissue specimen; an embedding medium; a freezing plane for providing direct metal contact freezing of the specimen; a knife blade comprising a cutting edge which is substantially parallel to and may be displaced a preset distance from the freezing plane; and driving means for transporting the block holder towards the freezing plane for creating a flat frozen surface of the specimen having a frozen thickness t and also for transporting the frozen specimen past the knife edge to provide a section having a desired thickness. The planar relationship between the freezing plane and the cutting edge together will provide information of the frozen thickness t of the specimen, and allows for precise and automated movement of the clamped block holder for trimming. The freezing plane is preferably cooled to at least −60° C. by any of several means. The use of two mating wedge washers are preferably provided at the freezing station to enable a proper parallel orientation between the cutting plane and the freezing plane.

BRIEF DESCRIPTION OF THE DRAWINGS

While the specification concludes with claims particularly pointing out and distinctly claiming the subject matter regarded as the invention herein, it is believed that the present invention will be more readily understood upon consideration of the following description taken in conjunction with the accompanying drawings, wherein:

DETAILED DESCRIPTION OF THE DRAWINGS

Figure 1:
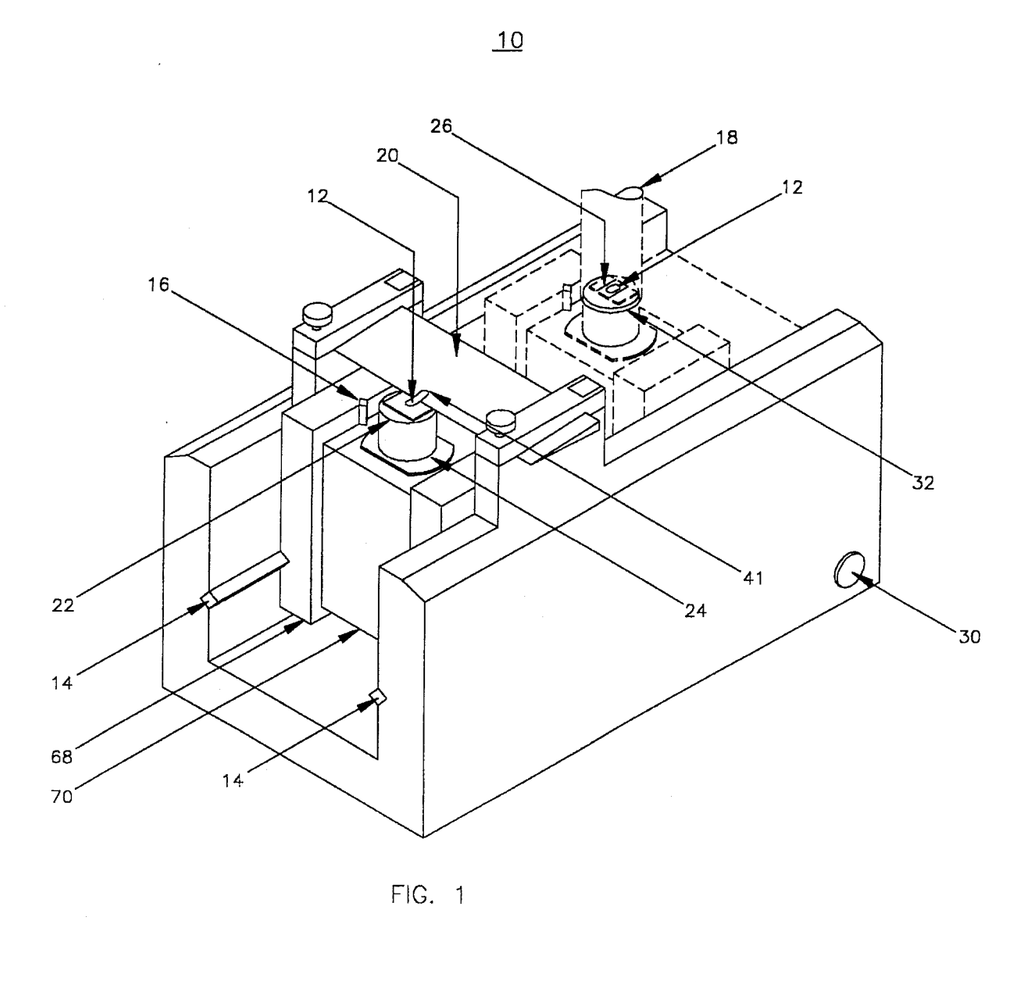
FIG. 1 is a perspective illustration of the apparatus of the present invention including a sliding microtome and a freezing station.

Referring first to FIG. 1, the semi-automated apparatus of the present invention, generally designated 10, is shown. Apparatus 10 is capable of moving a specimen 12 in both a Y-axis direction and a Z-axis direction as orientated in FIG. 1. Movement in the Y direction is controlled along two Y guide elements 14 and movement along the Z direction is controlled by two Z guide elements 16.

In FIG. 1, for illustrative purposes, specimen 12 on a block holder 22 is shown (in phantom) at a freezing station 18 and in its cutting mode at a knife 20. Of course, in actuality, the same specimen would first be frozen at a freezing station 18, then repositioned to be cut by knife 20.

Figure 2:
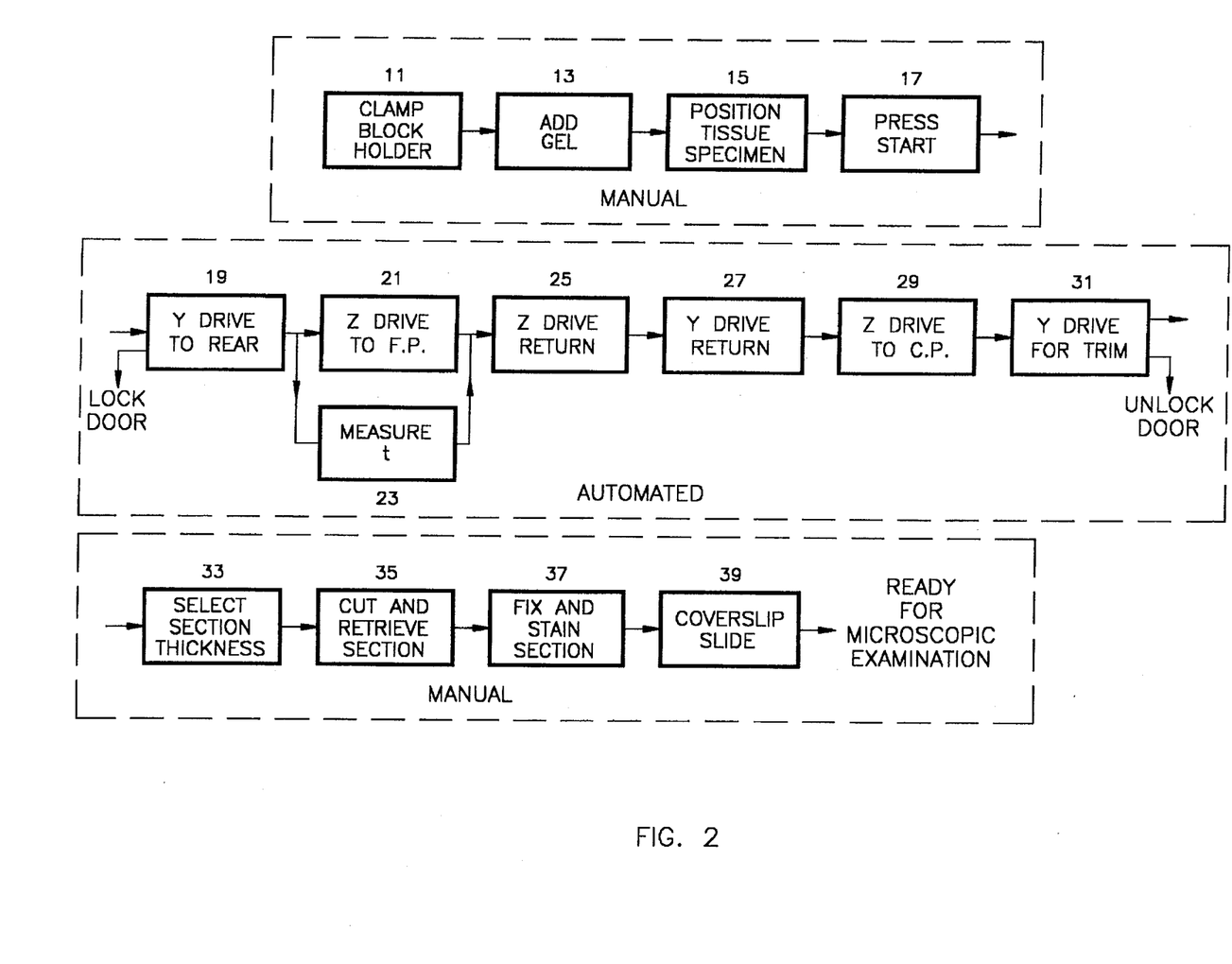
FIG. 2 iS a system block diagram of the preferred embodiment of a system of the present invention.
Figure 3:
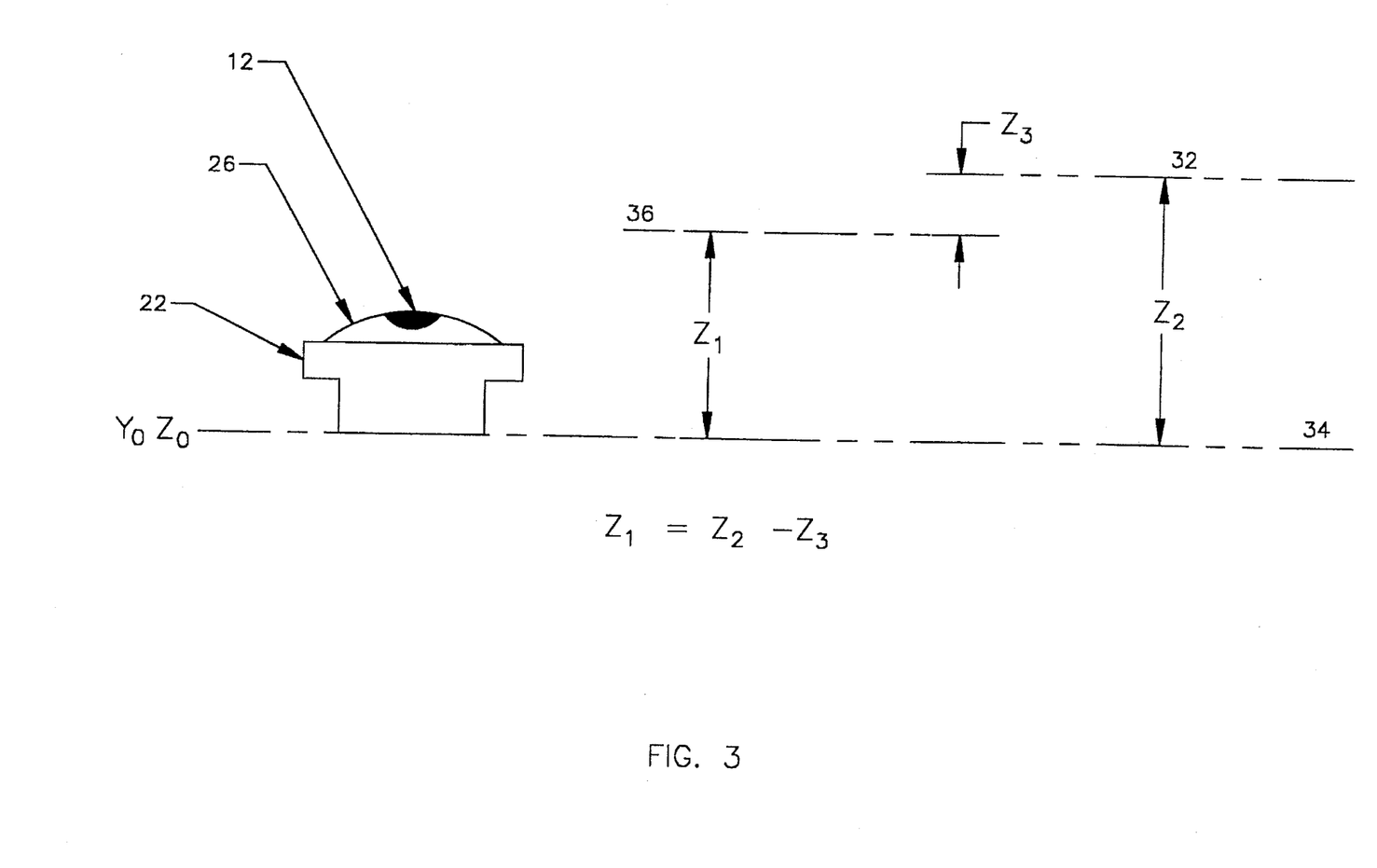
FIG. 3 is a schematic illustration of the spatial relationship between the datum (reference) plane, the freezing plane and the cutting plane of the present invention.

The block flow chart diagram of FIG. 2 illustrates the steps of the present invention. The understanding of each of these steps is facilitated by reference to the spatial relationships between the elements shown in FIGS. 3 and 4. First, in step 11, block holder 22 is secured by a clamp 24 (as shown in FIG. 1). Next, an embedding medium 26 is dispensed onto the surface of block holder 22 (step 13). Embedding medium 18 is preferably a viscous gel. Then, the tissue specimen 12 is positioned on top of embedding medium 26'(step 15). A start button 30 on apparatus 10 is then activated (step 17). Obviously, the steps up to this point require some, although minimal, manual operation.

Figure 4:
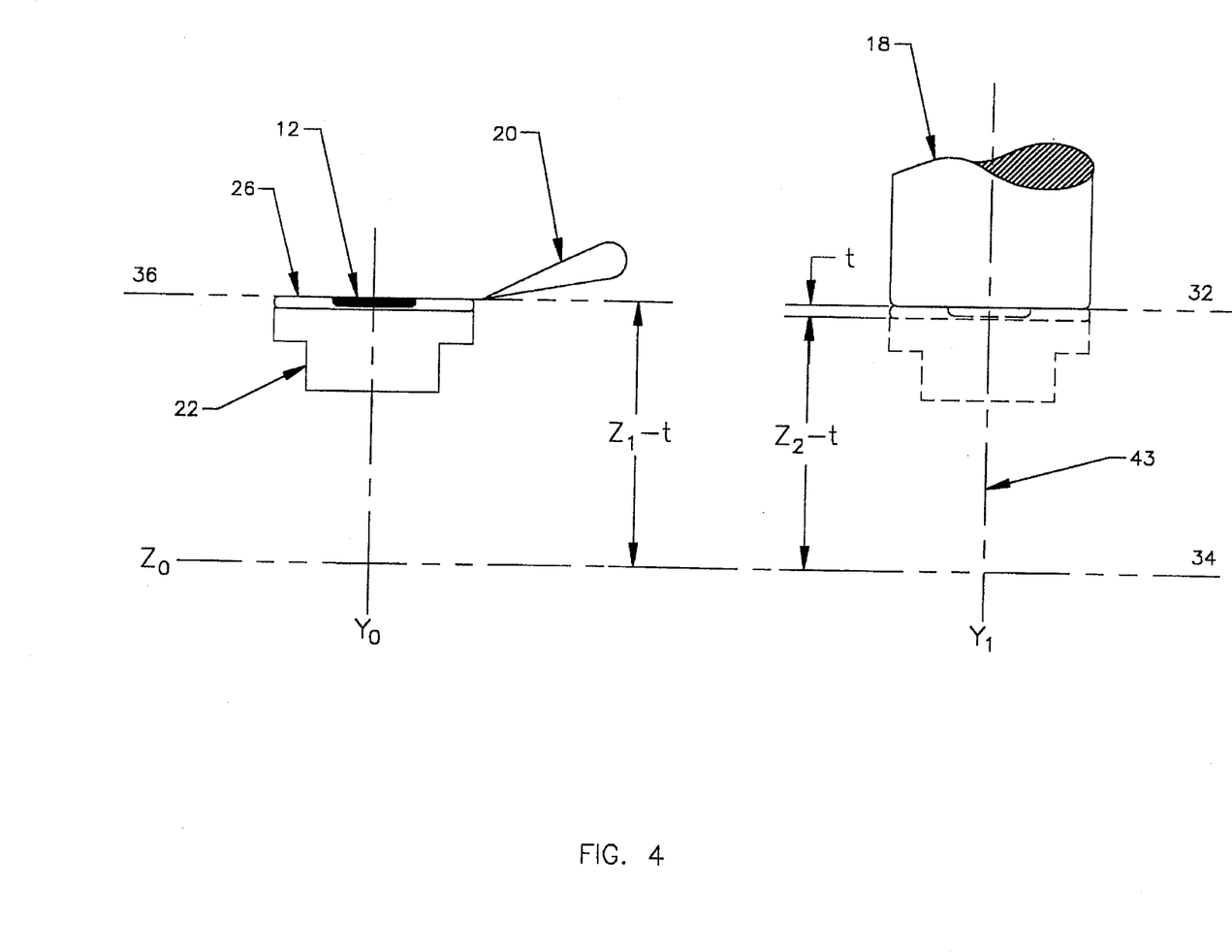
FIG. 4 is a functional schematic illustration of the spacial relationships between the datum plane, the freezing plane and the cutting plane of the present invention similar to FIG. 3 but including schematic illustrations of the freezing station, block holder and embedded specimen.

The steps in the middle portion of FIG. 2 are automated functions. After the door (not illustrated) enclosing apparatus 10 is locked, block holder 22, which contains embedding medium 26 and specimen 12 is driven to the rear of apparatus 10 (step 19). This Y position is defined in FIG. 4 as position $Y_1$, a centerline 43 of freezing station 18. This travel of a Y table 68 in the Y direction is precisely controlled along Y guide elements 14. A stepper motor/encoder 80 (to be described in more detail hereinafter) drives a Z table 70 with clamped tissue specimen 12 to a freezing plane 32 as shown in FIG. 4 (step 21). The surface of freezing station 18 is at a distance $Z_2$ from a datum plane 34 ( defined by Y guide-elements 14) and is precisely parallel to datum plane 34. As shown in FIG. 4, the edge of knife 20 is at a cutting plane 36 which is also parallel to datum plane 34 and freezing-plane 32. In addition, the distance between cutting plane 36 and freezing plane 32 is also fixed ($Z_3$). Thus, for any given thickness of tissue specimen 12 and embedding medium 26, the final thickness, t, of the frozen tissue 12 and medium 26 can be determined from the relationship:

$$t = Z_2 - Z_{(actual)}$$

where $Z_{(actual)}$ is defined (and measured) as the distance that Z table 70 is advanced toward freezing plane 32 until freezing stalls the Z drive.

Figure 6A:
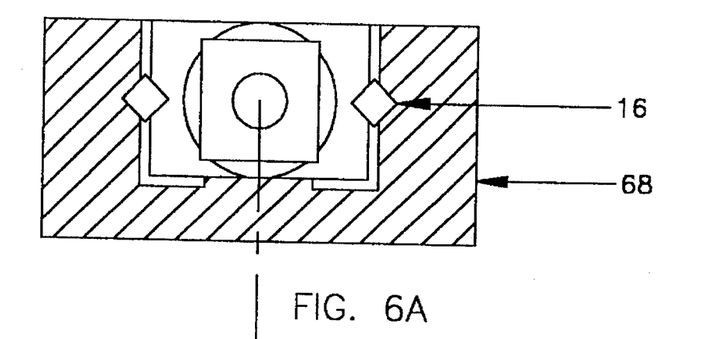
FIGS. 6A and 6B are top and side view cross sectional illustrations of the Z table of the present invention.
Figure 6B:
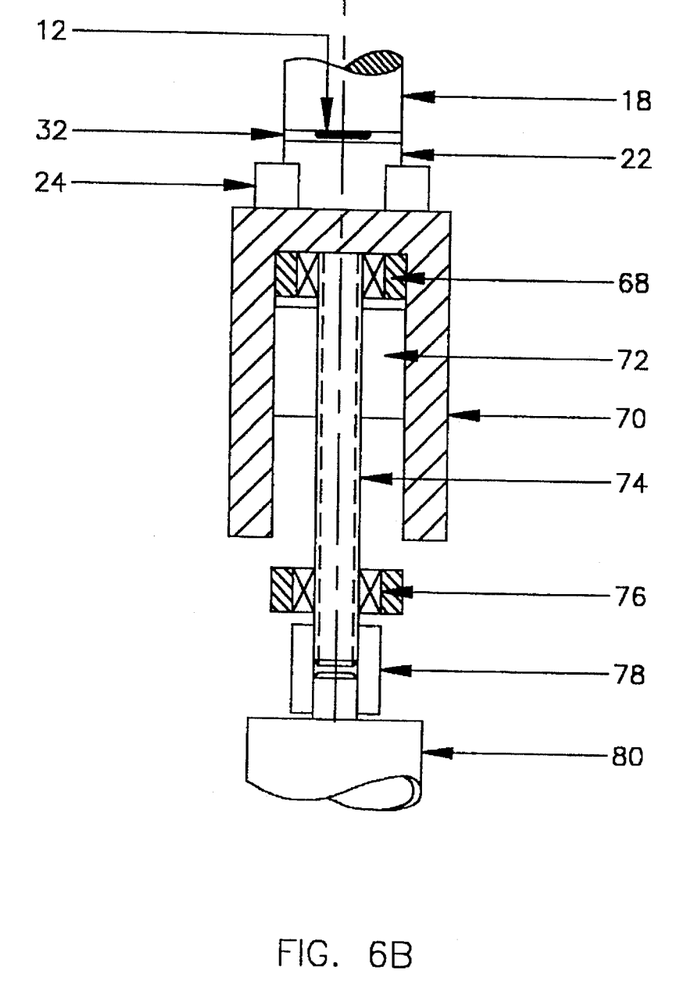

The calculation of frozen thickness t (step 23) is accomplished by measuring the travel $Z_{(actual)}$ that occurs when the Z drive advances the specimen towards freezing plane 32 until freezing stalls the Z drive. One type of motor that can be used for this measurement is stepper motor/encoder 80 (FIG. 6) which can count how many steps are necessary to travel between datum plane 34 and freezing plane 32. A lead screw 74 is turned to incrementally drive the Z table 70 toward freezing plane 32. The preferred and novel freezing technique to be used in the present invention will be described with detailed calculations as an illustration of how the thickness of t can be established using the following known parameters:

| | |
|---|---|
| Number of steps per revolution: | 100 |
| Mechanical lead screw 17 revolutions per inch: | 40 or .025"/rev. |
| Coupling between lead screw 74 and stepper motor/encoder 80: | Direct(1:1) |

With such parameters, the travel for each step can be determined: 1 step=1/100 Rev×0.025"/Rev×25400microns/in. Then:

| | |
|---|---|
| 1 step | 6.35 microns. |

Each step can further be divided into 8 micro steps:

| | |
|---|---|
| 1 microstep = | 6.35/8 = 0.79 microns |
| 1 inch travel = | 40 × 100 × 8 |
| 1 inch travel = | 32,000 microsteps. |

Thus, in the example shown, $Z_2$=32,000 microsteps. The travel $Z_{(actual)}$ can be measured as a number of steps. Thus, if $Z_{(actual)}$=30,000 microsteps, then t=32,000−30,000 =1562.5 microns or 0.0625 inches. Of course, the numbers provided are exemplary and similar calculations can be made to permit the measurement of any thickness t, within the limitations of the device.

After a measurement of frozen thickness t is made, the clamped specimen 12 is driven back along the Z-axis (step 25) and the Y-axis (step 27) to its starting position $Z_0$, $Y_0$. Once back in its starting position, the clamped embedded specimen 12 is driven along the Z-axis a distance $Z_1$−t toward the cutting plane (step 29). This places the flat surface of specimen 12 coincident with cutting plane 36. An additional upward movement in the Z direction (also represented by step 29) is required to obtain a desired trim thickness. This trim thickness is set by the operator in advance, and is automatically added to the Z drive. The clamped section is then driven in the Y direction (step 31) to permit the cutting of specimen 12 and its surrounding embedding medium 32 by knife 20 as block holder 22 passes by the edge of knife 20 to form a section 41. The device is then driven back, in the Y direction, to its starting position, $Y_0$ (part of step 31). It will be appreciated by those skilled in the art that during the return stroke to the starting Y-axis position, the Z-axis may be driven downward several microns to prevent grazing of the surface of the block face 22 by the edge of knife 20. This non-grazing feature on the return stroke, is generally referred to as a "retracting" microtome. The door to apparatus 10 is then unlocked.

The bottom portion of the block diagram of FIG. 2 again represents manual steps. In essence, the operator visually inspects the cut surface. If section 41 is inappropriate, the operator can obtain another section by selecting the same or a different section thickness (step 33) and repeating at least steps 29 and 31. The final three manual steps shown in FIG. 2, namely, (i) the cut-retrieve section step 35, (ii) the fix and stain section step 37; and (iii) the coverslip slide step 39 are well understood in the art and will not be described herein.

The novel sliding-type apparatus 10 for freezing and cutting the tissue specimen provides accurate cutting and measuring by carefully defining, in advance, the distance between datum plane 34, freezing plane 32, and cutting plane 36 of the apparatus.

Figure 5A:
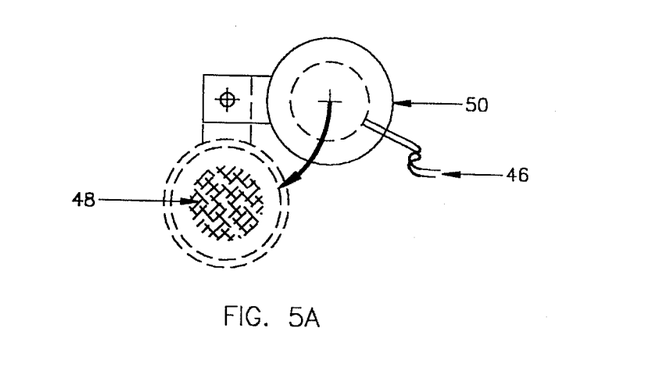
FIGS. 5A–C are partial cross sectional illustrations of the freezing station of the present invention and illustrate the use of wedge washers to permit precise axial and angular adjustments of the freezing plane in the apparatus of the present invention.
Figure 5B:
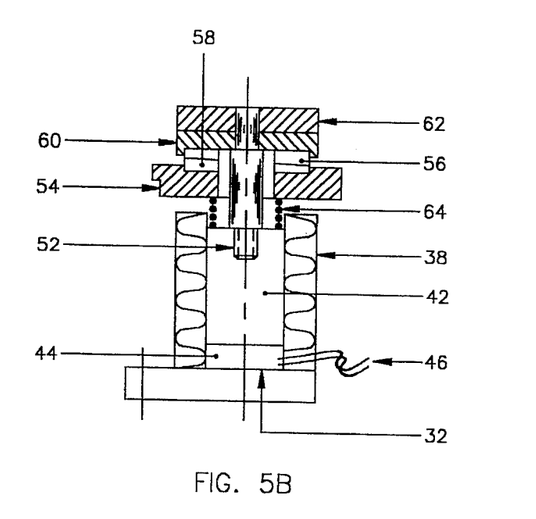
Figure 5C:
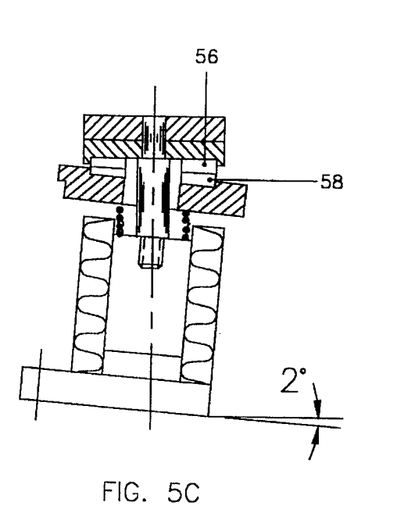

FIGS. 5A–5C demonstrate one means to adjust the height and angular position of the freezing plane 32 so that it is at the correct distance $Z_2$ from the datum plane 34 and parallel to the cutting plane 36. Freezing station 18 is insulated over most of its surface, by a thermally insulating material 38, except the circular downward facing freezing plane 32. Refrigerant inlet and outlet lines used to maintain a freezing block 42 at the desired low temperature will be shown in detail in FIGS. 8 and 9. The freezing station 18 may be cooled to an even lower temperature by use of a single or multi-stage thermal electric cooler (TEC) 44 powered by electrical cables 46 and with its "hot" side cooled by mechanical refrigeration means (described in detail henceforth). Alternatively freezing station 18 may be cooled by a bath of liquid nitrogen or by a slurry bath of dry ice and a suitable low temperature freezing point fluid such as acetone. Freezing plane 32 is normally covered by a spongy material 48 which is maintained dry or alternatively which may be maintained in a wet condition with a low temperature fluid such as a methanol-ethanol mixture. Spongy material 48 is supported by a moveable shutter 50 which normally covers freezing plane 32. Just prior to the freezing event, shutter 50 is swung out of the way to expose freezing plane 32.

If freezing station 18 is maintained at a temperature of −50° C. or colder, spongy material 48 may be used dry. When shutter 50 is swung out of the way, if a wet spongy material is used, a thin layer of fluid may remain on freezing plane 32. After the freezing step, shutter 50 is moved back into position covering freezing plane 32. With shutter 50 in place, the traces of water vapor in the air are prevented from contacting freezing plane 32 and little or no undesirable frost builds up.

A shaft 52 which is rigidly secured to freezing block 42 passes through an oversized hole defined by a structure 54 and through two wedge shaped washers 56 and 58. The end of shaft 52 is threaded into two nuts 60 and 62. The lower nut 60 is used to adjust the height of freezing block 42 relative to structure 94. A compression spring 64 is used to provide a downward force to freezing block 42.

If freezing plane 32 is not initially parallel to cutting plane 36, an angular adjustment can be made by rotating the lower wedge washer 56 relative to the upper wedge washer 58. In FIG. 5B, wedge washers 56 and 58 are shown exactly opposed to one another and the angular adjustment is 0°. In FIG. 5C, the two wedge washers 56 and 58 are shown with their wedge angle of 1 degree in the additive position (i.e., the two high points are aligned) giving a total of two degrees angular adjustment. FIG. 5C is shown with exaggerated angles for clarity. The two wedge washers 56 and 58 can be rotated to any intermediate position between zero and the maximum shown, to yield an angular correction between 0 and 2 degrees over a 360° range. After all the adjustments are made, lock nut 62 is secured at the desired adjustment. The magnitude of the adjustment shown in FIG. 5C is one degree per wedge. Wedge washes having larger (or smaller) angles can be used to increase (or decrease) the adjustment range.

Thermoelectric cooler 44 is thermally coupled to freezing block 42. When a D.C. voltage is applied to electric cables 46, one side of TEC 44 becomes hot and the other side of TEC 44 becomes cold. The hot side is cooled by freezing block 42 and the cold side may be 20° to 40° C. colder. Thus, under steady state conditions, if the "hot" side of freezing block 42 is maintained at −40° C. by mechanical refrigeration means, TEC 44 may generate a "delta T" (i.e., the temperature difference between the hot and cold sides of TEC 44) of between 20° and 40° C. Under these conditions, the freezing plane 32 will be −60° C. to −80° C. The D.C. voltage can be reversed at any time, to heat the cold surface and thereby reduce or eliminate frost build-up.

FIGS. 6A and 6B show a top view and side view respectively of a cross section of Z table 70 driven by stepper motor/encoder 80. Stepper motor/encoder 80 is directly coupled to lead screw 74 by a coupling 78. Lead screw 74 can turn in precision ball bearings 76 housed in Y table 68. Rotation of lead screw 74 causes a drive nut 72 to advance linearly up or down depending on the direction of rotation. Drive nut 72 is fastened to Z table 70 which houses clamp 24 in which the block holder 22 is secured.

In FIG. 6B, Z table 70 is shown near its uppermost position with tissue specimen 12 and embedding medium 26 flattened against freezing plane 32. The final thickness, t, of the frozen specimen 12 and surrounding embedding medium 26 can be established from the number of steps made by stepper motor/encoder 80. In a preferred embodiment, lead screw 74 has 40 threads per inch and one revolution advances Z table 70 by 0.025 inches. Each step of the stepper motor/encoder 80 is divided into 100 steps for one revolution (3.6 degrees per step). There are 8 microsteps per step for a total of 32,000 microsteps (40×100×8) per inch travel of Z table 70. Thus, if the actual number of microsteps $[Z_{(actual)}]$ from datum plane 34 to freezing plane 32 was 30,000 and $Z_2$ is known to be 32,000 microsteps, the thickness, t, is the difference (2,000 microsteps). Since each microstep is 0.79 microns, 2,000 microsteps is 1,562.5 microns or .0625 inches.

Block holder 22 then can be driven back to its starting position $Z_0$, $Y_0$. Since the distance $Z_1$ between datum plane 34 and cutting plane 36 is known, the Z table 70 can then be advanced a distance $Z_1$−t, corresponding to the cutting plane 36. The predetermined Z drive advance for the section thickness followed by a four-aft drive of Y table 68, will cause knife 20 to cut material from freezing plane 32. The user visually verifies that the block face is adequate (i.e., a desired surface has been exposed by the cut). Z table 70 can now be advanced again by the desired section thickness (typically between 2 and 6 microns). Y table 68 is then driven through another fore-aft cycle to produce a section of specimen 22. The user then retrieves the section onto a slide by any of several means, and after fixation, staining and cover-slipping, the slide is ready for microscopic examination.

The mass of freezing station 18 is preferably several hundred times the combined mass of specimen 12, block holder 22, and embedding medium 26. By use of direct metallic contact, specimen 12 and embedding medium 26 can be snap-frozen in 8–10 seconds at a near constant freezing rate. The ice crystal size is strongly influenced by the temperature at freezing plane 32, the rate of freezing, and where section 41 was cut relative to freezing plane 32. Acquiring section 41 at or close to freezing plane 32 yields the smallest ice crystals. When specimen 12 and embedding medium 26 are brought in contact with freezing plane 32, the combined specimen 12 and embedding medium 26 both flatten somewhat. The amount of flattening will be dependent upon many variables including, but not limited to, the size and type of specimen, the amount of embedding medium 26 used and its temperature just prior to contact, the velocity of movement when contact occurs, and the contact pressure between specimen holder 22 and freezing plane 32. Up to certain internal pressure limitations, dependent on the type of tissue being sampled, tissue specimen 12 can be safely flattened out. The resulting flattened frozen specimen 12 has a correspondingly larger area for diagnostic evaluation for any given size and type of specimen, than an unflattened specimen. In addition, flattened specimen 12 has lower thermal resistance than the same volume of thicker tissue. As a result, ice crystal size will be smaller, on average, than with unflattened tissue, and the overall quality of section 41 will be improved. In essence, a larger face area enables the pathologist to see more of the tissue and, with less ice crystal damage in any given section.

In addition to flattening the tissue, the controlled pressure of direct metallic freezing has a beneficial effect on the rate of freezing. During the first few milliseconds, when the surface in direct contact with freezing plane 32 freezes, and a hard ice layer forms at freezing plane 32, the transformation from a gel-like surface (a combination of specimen 12 and embedding medium 26) into a hard noncompliant surface, abruptly changes the contact area between the frozen layer and freezing plane 32, due to the shrinkage that occurs with freezing. This reduced contact area could slow down the rate of heat transport between the unfrozen tissue below the frozen layer and freezing plane 32. A controlled pressure between specimen 12 and freezing plane 32 reduces this effect. Stepper motor/encoder 80 can be controlled such that its stall torque can deliver a specified maximum force at freezing plane 32. When the other variables are controlled, the pressure at freezing plane 32 is proportional to the torque of stepper motor/encoder 80. This controlled pressure improves the heat transfer between specimen 12 and freezing plane 32 and results in smaller ice-crystals. The controlled pressure can also determine the final thickness t of the frozen specimen.

In practice, a needle biopsy can yield a specimen 12 that is pin-head size. When such a specimen in frozen, it is critical to minimize trimming since there is so little of the specimen to start with. In conventional methods, it is not unusual to deplete up to half the original specimen before an adequate section 18 is obtained. The reduced trimming requirements of the present invention reduces the risk of tissue depletion of specimen 12. As a further advantage of the snap-freezing technique of the present invention, it has been found that when specimen 12 is brought in contact with freezing plane 36, and freezing occurs, the layer in direct contract with freezing plane 36 normally adheres to the surface of freezing plane 36 if the surface of freezing plane 36 is −40° C. or warmer. The use of freezing station 18, whose surface is −50° C. or colder, prevents or greatly reduces the adhesion of specimen 12 and/or embedding medium 26 to freezing plane 32.

It is the inherent simplicity of the present invention which results in its advantages. In effect, once the distance $Z_2$ between freezing plane 32 and datum plane 34 and the distance $Z_3$ between freezing plane 32 and cutting plane 36 are established, and a means is provided in which to measure $Z_{(actual)}$, which is the distance Z table 70 travels, section 41 can be automatically cut and subsequently examined. The frozen specimen thickness t can be determined from the known values of $Z_1, Z_2, Z_3$. Thus, for any specimen thickness, the thickness of the flattened and frozen specimen can be determined, and a section at or close to the freezing plane can be retrieved.

The actual step of freezing specimen 12 and embedding medium 26 will be described in detail in connection with FIGS. 7–9. However, before turning to the novel freezing system utilized in the present invention, a brief understanding of a prior art cascade freezing system should be described. In such prior art cascade systems, there are typically two refrigerants incorporated. One refrigerant such as DUPONT product #HP62 is used to cool a second refrigerant down to a low temperature, typically in the range of −30° to −40° C. The second refrigerant such as DUPONT product #F23 becomes a liquid at this low temperature and is able to cool a load to a considerably lower temperature, typically −70° to −80° C. The two refrigerants are usually kept separated from each other, thus requiring separate condensing units.

Figure 7:
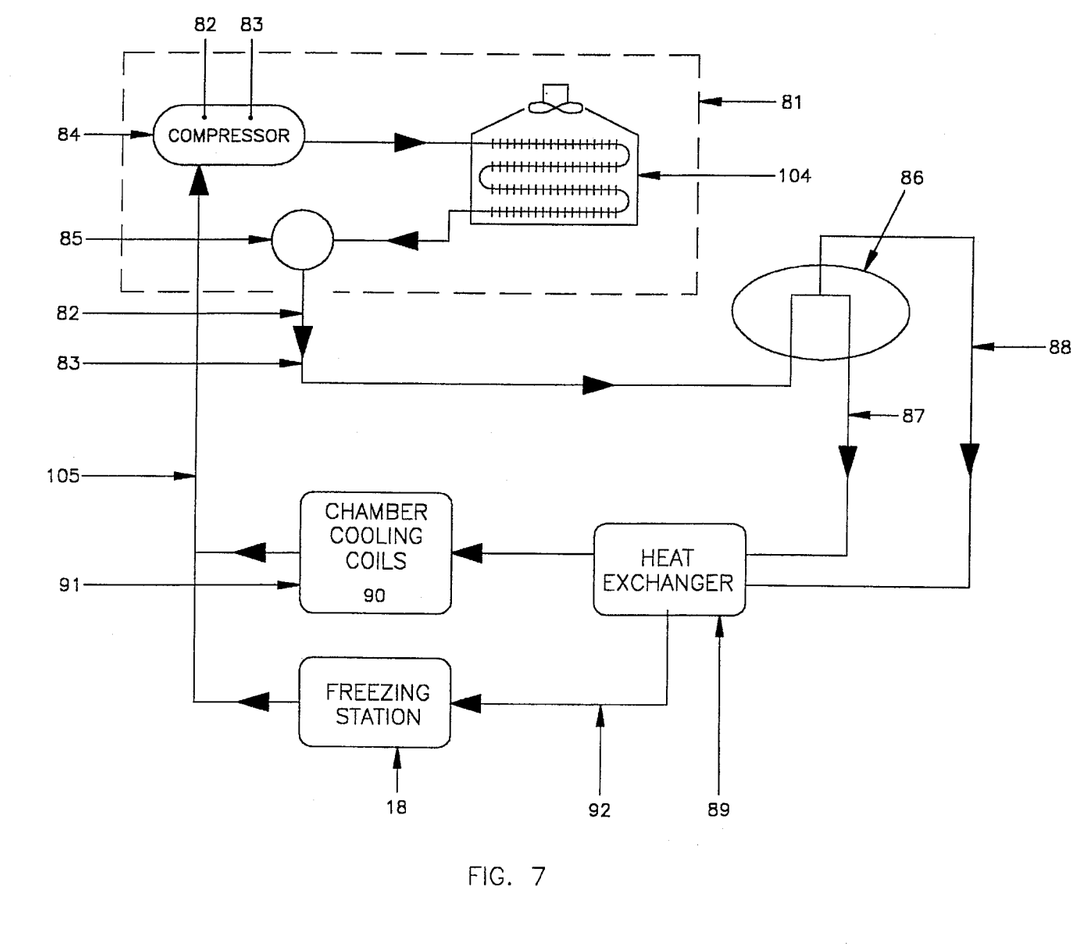
FIG. 7 is a schematic diagram of a single compressor two refrigerant system used in conjunction with the present invention.

FIG. 7 is a schematic of a novel system implementing two refrigerants used with a single condensing unit 81. The single compressor, two-refrigerant scheme of the present invention behaves like a conventional two-compressor cascade system, but with considerable savings in cost, weight, and bulk. In this novel system, refrigerants 82 and 83 are compressed to the same pressure in a compressor 84. However, due to the differences in their boiling points, after passing through a condenser coil 104 and through a receiver 85, refrigerant 82 exits receiver 85 as a liquid and refrigerant 83 exits as a gas. At a debubbler 86, the gas bubbles are separated from the liquid and refrigerant 82 flows (as a liquid) through a line 87 and refrigerant 83 (as a gas) passes through a line 88 to a heat exchanger 89. In heat exchanger 89, refrigerant 82 is converted to a gas and thereby cools the entire heat exchanger 89. Refrigerant 83, which enters heat exchanger 89 as a gas, is also cooled down and exits as a liquid. Liquid refrigerant 82 is arranged to flow countercurrent with gas refrigerant 83.

Liquid refrigerant 83 is transported from heat exchanger 89 to freezing station 18 by a line 92. Inside freezing block 42, which is part of freezing station 18, liquid refrigerant 83 is converted to a gas thereby cooling freezing station 18 to its operating temperature of typically −70° to −80° C. The still cold refrigerant 82 exits heat exchanger 89 and flows into cooling coils 90 which are used to cool down a cryostat chamber 91. Refrigerant 82 and refrigerant 83, now both gases, then return to compressor 84 through a line 105 to allow the entire cycle to be repeated. It should be noted combinations of different refrigerants can be used to shift the operating points downwards or upwards.

Figures 8A, 8B, 8C:
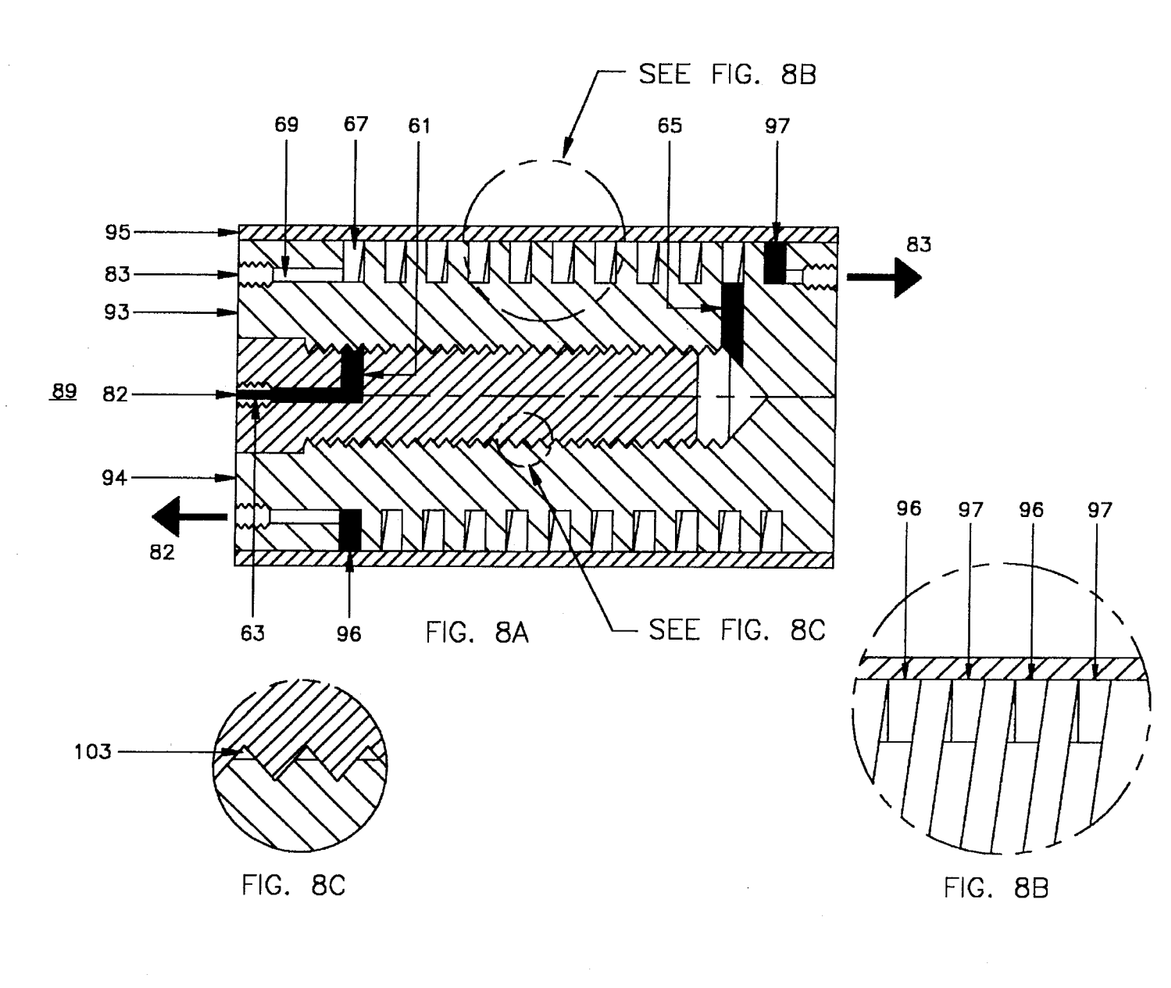
FIG. 8A is a cross section of the heat exchanger shown in FIG. 7 with certain portions in exploded detail in FIGS. 8B and 8C.

FIG. 8 is a cross section of heat exchanger 89. In FIG. 8, heat exchanger 89 is preferably made of a high thermal conductivity material such as brass, and is approximately 2.5 inches in diameter and 3.5 inches in length. Refrigerant 82 enters a central threaded element 93 as a liquid via a threaded fitting (not shown). A radial hole 61 through the first thread of threaded element 93 intersects a hole 63 that communicates with the fitting in the central threaded element 93. The tips of the threads of threaded element 93 are truncated as shown in the enlarged detail of FIG. 8C to form a helical capillary pathway 103 for refrigerant 82. The hydraulic resistance of capillary pathway 103 will determine the suction pressure at which the system will operate. At the end of the threads of element 93, there is another radial hole 65 that is in communication with one of a pair of helical slots 96 and 97 cut into the perimeter of a core 94. A sleeve 95 encloses core 94. Refrigerant 82 flows along the capillary pathway into helical slot 96 (FIG. 8B) and finally out the exchanger as a gas.

In operation, refrigerant 83 enters heat exchanger 89 as a gas via a threaded fitting (not shown). A radial hole 67 in the lowermost end of helical slot 97 (FIG. 8B) intersects an axial hole 69 that communicates with the threaded fitting. As refrigerant 83 progresses through heat exchanger 89, its temperature drops to approximately −40° C. and refrigerant 83 exits from heat exchanger 89 as a liquid. The ends of sleeve 95 and ends of threaded element 93 are sealed to core 94 by soldering or other suitable means to prevent loss of either refrigerant 82 or refrigerant 83. The central portion of core 94, which contains the helical slots, are shrunk fit into sleeve 95 to prevent cross flow between refrigerants 82 and 83.

Figure 9:
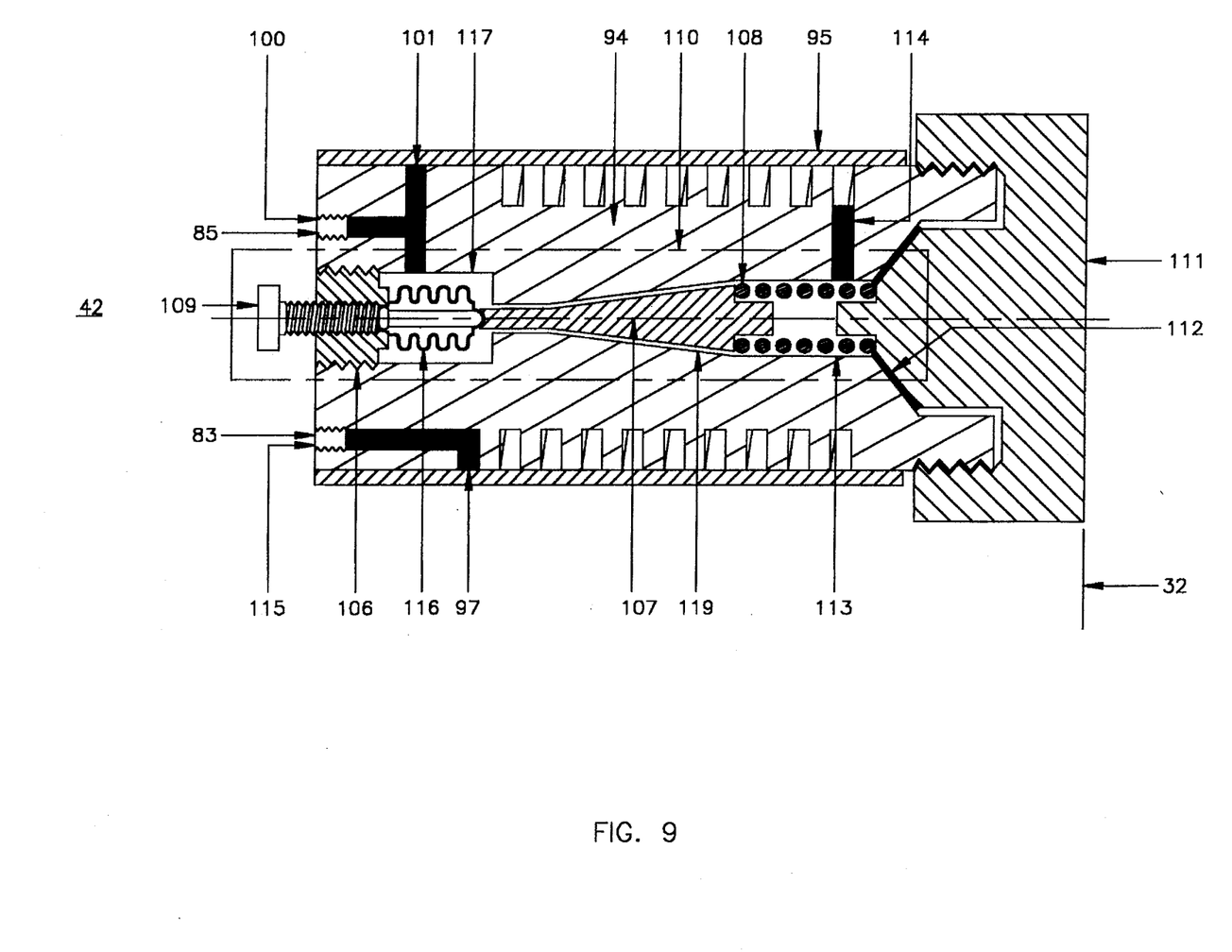
FIG. 9 is a cross section of the freezing block with an integrated expansion valve utilized in the present invention.

FIG. 9 is a cross section of freezing block 42. Its construction is similar to that of heat exchanger 89 except that there is only a single helical slot 97 and the capillary pathway 103 is replaced by an integrated automatic expansion valve 110. Expansion valve 110 uses negative feedback to control the pressure at the suction side (the low pressure side). Capillary pathway 103 may generate the same hydraulic resistance as expansion valve 110 but cannot respond to changes in the temperature of the load. By maintaining the same suction pressure for various loads, expansion valve 110 can change the flow of refrigerant 83 in response to a change in load.

Expansion valves are generally sold as separate components. Since the output of the expansion valve is the cold gas, the refrigerant line exiting from the valve is very cold and subject to frost build up. In order to minimize losses, the expansion valve must be placed very close to the load. In FIG. 9, expansion valve 110 is an internal portion of freezing block 42 and thus eliminates all the energy losses and any possibility of frost build up associated with a separate expansion valve.

The incoming refrigerant 83, in liquid form, enters freezing block 42 at an inlet port 100. A radial hole 101 near the entry point communicates with the exterior surface of a bellows 116. One end of bellows 116 touches an actuator 107. The other end of bellows 116 is sealed to a plug 106 on which there are pipe threads to seal it to core 94. The central portion of plug 106 contains a threaded spring plunger 109 which is in line with actuator 107 but inside bellows 116. The actuator 107 has a portion of its length which is tapered (at approximately a 6° angle). The large end of the tapered length of actuator 107 has a control spring 108 which forces the tapered length into its matching tapered hole 119 in core 94. The other end of control spring 108 is seated in end cap 111 which constitutes part of freezing block 42. The end cap 111 is sealed to the core 94 using a conventional copper ring seal 112.

Control spring 108 delivers a force to actuator 107 which just balances the incoming fluid pressure acting on bellows 116 and actuator 107. The pressure acts against the projected area of the actuator 107 and tends to move actuator 107 in a direction to permit more fluid to flow in. The force of spring 108 exactly balances the force from the fluid pressure and an equilibrium condition exists whereby actuator 107 is seated in its mating tapered hole 119 in core 94, and no fluid flows.

Adjustment spring plunger 109 can now be rotated to increase the force on the end of bellows 116 thereby changing the equilibrium condition and actuator 107 moves towards the large end of tapered hole 119, permitting liquid refrigerant 83 to flow into the annular space between actuator 107 and tapered hole 119 in core 94. This space is exceedingly small and the entering refrigerant 83 experiences a substantial drop in pressure, sufficient to cause it to turn into a gas which flows into a region 113 at control spring 108. There is a radial hole 114 between helical slot 97 and region 113, providing a pathway for the gas to flow into helical slot 97 and ultimately out through exit port 115.

Spring plunger 109 can be adjusted to optimize the temperature/flow rate conditions that are best suited for the load and the temperature range over which the load operates. Thus, as the heat gain or loss varies, the pressure at the suction side will remain essentially constant.

In operation, refrigerant 83 enters freezing block 42 as a liquid at inlet port 100, and flows into an annular space 117 exterior to bellows 116, then into tapered hole 119. The high hydraulic resistance of this pathway causes the pressure of refrigerant 83 to drop causing refrigerant 83 to boil off into a gas, thereby reducing the temperature of core 94 to approximately −82° C. In order to achieve these very low temperatures, it is necessary to operate at or near atmospheric pressure. A typical low temperature refrigerant, such as DUPONT® Product No. F23™ can be used which has a boiling point of −82° C. at atmospheric pressure. At these very low pressures, the flow rate is very low and consequently, the cooling capacity is also very low. Since freezing block 42 is a relatively small mass (typically 2–3pounds) and is well insulated to reduce its heat gain, the low cooling capacity is still adequate.

Expansion valve 110, which has been described as a pressure controlled expansion value, can be replaced with a thermostatic expansion valve. From a functioning standpoint, a thermostatic expansion valve also can control the flow of a refrigerant. However, unlike a pressure control expansion valve, the thermostatic expansion valve detects a change in temperature, and not pressure. From a component standpoint, spring plunger 109 would be replaced with a capillary tube that is sealed into plug 106. The other end of the capillary tube has a sensing bulb to sense the temperature of the load. A rise in the temperature of the load would cause gas in the sensing bulb to expand. Bellows 116 would expand in response to this resultant increase in pressure, causing actuator 107 to move and thereby allowing additional refrigerant to flow.

By using the novel system and method described herein, an effective and high quality tissue section can be obtained for medical diagnostic purposes.

It would be apparent from the foregoing description that the present invention provides a new and improved system and method for freezing and cutting a tissue specimen for medical and laboratory diagnostic purposes. While the preferred embodiment has been described, other variations are possible. For instance, the device of the present invention has been described in connection with the cutting of human or animal tissue, however, other materials such as plants and insects can be cut in such a fashion.

While there has been shown and described what is presently considered to be the preferred embodiment of this invention, it would be apparent to those skilled in the art that various changes and modifications may be made without departing from the broader aspects of this invention. For instance, although a stepper motor has been incorporated to control movement along the Z-axis, other driving means, perhaps computer guided controls, are possible. It is, therefore, aimed in the appended claims to cover all such changes and modifications as fall within the spirit and scope of the invention.

I claim:

1. An integral apparatus for freezing a specimen and for cutting a section therefrom having a predefined Y-axis and Z-axis comprising:

a specimen block holder for holding said specimen;

a freezing plane orthogonal to the Z-axis for providing direct metal contact freezing of said specimen;

a microtome slidable in the Y-axis direction and including a knife positioned at parallel distance $Z_3$ in the Z-axis direction from said freezing plane;

Z-axis driving means for transferring said block holder from said freezing plane to a position displaced from said knife by a preselected section thickness along the Z-axis; and Y-axis driving means for transporting said block holder in a Y-axis direction so that said knife cuts said section from said specimen having said preselected section thickness, 2. The apparatus of claim 1 wherein said specimen is disposed within an embedding medium, 3. The apparatus of claim 1 further comprising a pair of Y-axis guide elements for controlling movement of said specimen block in the Y-axis direction.

4. The apparatus of claim 3 further comprising a pair of Z-axis guide elements for controlling movement of said specimen block in a Z-axis direction.

5. The apparatus of claim 4 wherein said Z-axis driving means comprises a stepper motor/encoder for driving and measuring movement in the Z direction and having a preset stall torque.

6. The apparatus of claim 5 wherein said pair of Y-axis guide elements define a Z-axis datum plane.

7. The apparatus of claim 6 wherein the Z-axis distance $Z_2$ between said datum plane and said freezing plane is predetermined.

8. The apparatus of claim 7 wherein the Z-axis distance $Z_1$ between said datum plane and said knife is predetermined.

9. The apparatus of claim 8 including means for calculating a final frozen thickness t of said section by subtracting the actual Z-axis movement, $Z_{(actual)}$, which is measured from said datum plane until said stepper motor/encoder stalls, from $Z_2$.

10. A method for freezing a specimen and for cutting a section therefrom in a cryostat chamber having a freezing station and a cutting station including the steps of:

a) providing a refrigerated freezing plane at said freezing station;

b) placing a knife blade whose edge defines a cutting plane in close proximity to said cutting station, said cutting plane being parallel to and a known distance from said freezing plane and said cutting station being an orthogonal distance Y, from said freezing plane;

c) defining a datum plane parallel to and a distance $Z_1$ from said cutting plane and parallel to and a distance $Z_2$ from said freezing plane;

d) placing said specimen on a block holder at the datum plane;

e) driving said block holder toward the freezing plane by means of a motor wherein said specimen is placed in direct contact with said freezing plane;

f) measuring a distance $Z_{(actual)}$ of said driving step when said motor stalls; and g) calculating a thickness t of the specimen when frozen at the freezing plane by subtracting $Z_{(actual)}$ from $Z_2$.

11. The method of claim 10 further comprising the step of:

h) returning said block holder to the datum plane.

12. The method of claim 11 further comprising the step of:

i) transporting said block holder toward said cutting station a distance of $Y_1$.

13. The method of claim 12 further comprising the step of:

j) driving said block holder a distance $Z_1$-t toward said cutting plane.

14. The method of claim 13 further comprising the step of:

k) further driving said block holder toward said cutting plane a distance equal to a desired section thickness.

15. The method of claim 14 further comprising the step of:

l) driving said block holder past said edge of said knife blade thus generating the section of said section thickness.

16. The method of claim 14 further comprising the step of:

m) reversing the driving step (l).

17. The method of claim 16 further comprising the steps of repeating steps (k) and (l).

18. A semi-automatic apparatus for freezing a specimen and for cutting a section therefrom comprising:

a metallic freezing plane;

a knife blade comprising a cutting edge which is substantially parallel to and displaced a preset distance from said freezing plane;

a block holder for holding said specimen; and driving means for transporting said block holder in a first direction so that said specimen is placed in direct contact with said freezing plane and in a second direction orthogonal to said first direction, for transporting said specimen across said cutting edge thereby forming said section.

19. The cryostat of claim 17 further comprising:

refrigeration means for cooling said freezing plane.

20. The cryostat of claim 19 wherein said refrigeration means includes a first refrigerant and a second refrigerant maintained in a single compressor.

21. The cryostat of claim 19 wherein said refrigeration means cools said freezing plane to a temperature at least as low as −60° C.

22. The cryostat of claim 18 wherein an exterior surface of said freezing plane is covered by a thermally insulating material prior to contact with said specimen.

23. The cryostat of claim 18 further comprising:

orientation coupling means at said freezing station for maintaining the substantial parallel orientation between said cutting edge and said freezing station.

24. The cryostat of claim 23 wherein said orientation coupling means comprises:

a first wedge washer having a angularly displaced plane; and a second wedge washer having an angularly displaced plane and overlaying said first wedge washer.

25. The cryostat of claim 18 wherein said driving means is a stepper motor/encoder providing signals used to calculate movement of said block holder.

26. The cryostat of claim 18 further comprising an embedding medium upon which said specimen is placed.

27. The cryostat of claim 18 wherein the embedding medium is a viscous gel.

28. A method for preparing a specimen for microscopic examination comprising the steps of:

freezing said specimen at a freezing station under a controlled pressure to provide a flat frozen surface of said specimen of thickness t;

transporting said specimen from said freezing station to said cutting station; and trimming said flat frozen surface to a desired section thickness at a cutting station comprising a knife edge at a fixed position which is parallel to said flat frozen surface.

29. The method of claim 28 further comprising the step of:

calculating thickness t prior to said trimming step.

30. The method of claim 28 further comprising the step of:

establishing a datum plane which is parallel to and known respective distances away from both said knife edge and said freezing station.

31. A freezing apparatus for cooling a freezing station comprising:

a compressor for storing a first refrigerant having a first boiling point and a second refrigerant having a second boiling point at an equal pressure;

a condenser coil coupled to said compressor to receiving said first and second refrigerants whereby said first refrigerant exits said condenser coil in a liquid state and said second refrigerant exits said condenser coil in a gas state;

means for transferring said first and second refrigerants from said condenser coil to a heat exchanger which converts said first refrigerant to a gas state thereby cooling said heat exchanger and converting said second refrigerant to a liquid state; and means for transporting said second refrigerant from said heat exchanger to a freezing block at said freezing station whereby said freezing station is cooled to a desired temperature.

32. The freezing apparatus of claim 31 in further comprising:

a debubbler coupled between said compressor and said heat exchanger, to separate said first and second refrigerants.

33. The freezing apparatus of claim 32 wherein said transferring means comprises:

a first line for transferring said first refrigerant from said debubbler to said heat exchanger; and a second line for transferring said second refrigerant from said debubbler to said heat exchanger.

34. The freezing apparatus of claim 31 further comprising:

feedback means for returning said first and second refrigerants back to said compressor after said freezing station is cooled.

35. A freezing block in a cryostat comprising:

an internal core;

an inlet port coupled to said internal core;

an integrated expansion valve for controlling flow of a refrigerant situated in said internal core; and an outlet port.

36. The freezing block of claim 35 wherein said expansion valve is a pressure controlled expansion valve.

37. The freezing block of claim 35 wherein said expansion valve is a thermostatic expansion valve.

38. The freezing block of claim 36 wherein said pressure controlled expansion valve comprises:

a tapered actuator having a large end and a narrow end;

an aunular tapered hole defined by the outer surface of said actuator and a correspondingly tapered internal structure of said valve surrounding said activator;

a bellows in communication with said inlet port and having a first end touching said narrow end of said actuator and a second end sealed to a plug in said internal core;

a spring plunger passing through a central portion of said plug and in alignment with said narrow end of said actuator, said spring plunger having one end extending externally from said freezing block and a second end inside said bellows and aligned with said narrow end of said actuator; and a control spring having one end seated in an end cap which is sealed to said internal core and a second end which exerts a force against said large end of said actuator.

39. The freezing block of claim 38 wherein said spring plunger is adjustable.

* * * * *